United States Patent
Boettcher et al.

(10) Patent No.: US 8,278,367 B2
(45) Date of Patent: Oct. 2, 2012

(54) SILICON MOULDING MATERIAL COMPRISING A TWO-STAGE HARDENING MECHANISM

(75) Inventors: Henrik Boettcher, Tostedt (DE); Stephan Neffgen, Hamburg (DE)

(73) Assignee: Ernst Muehlbauer GmbH & Co. KG, Norderfriedricskoog (DE)

( * ) Notice: Subject to any disclaimer, the term of this patent is extended or adjusted under 35 U.S.C. 154(b) by 132 days.

(21) Appl. No.: 12/515,083

(22) PCT Filed: Jan. 16, 2008

(86) PCT No.: PCT/IB2008/000092
§ 371 (c)(1), (2), (4) Date: May 15, 2009

(87) PCT Pub. No.: WO2008/059468
PCT Pub. Date: May 22, 2008

(65) Prior Publication Data
US 2010/0069526 A1    Mar. 18, 2010

(30) Foreign Application Priority Data
Nov. 16, 2006    (EP) .................................. 06023846

(51) Int. Cl.
*A61K 6/10*    (2006.01)
*C08L 83/04*    (2006.01)
(52) U.S. Cl. ........ 523/109; 523/105; 525/477; 525/478; 528/15; 528/18; 528/31; 528/32
(58) Field of Classification Search ...................... 528/10
See application file for complete search history.

(56) References Cited

U.S. PATENT DOCUMENTS

| | | | | |
|---|---|---|---|---|
| 4,808,649 | A * | 2/1989 | Gay et al. ....................... | 524/264 |
| 6,777,031 | B2 * | 8/2004 | Rocks ............................ | 427/387 |
| 2002/0147275 | A1 * | 10/2002 | Bublewitz et al. ............. | 525/100 |
| 2007/0026509 | A1 * | 2/2007 | Rogers et al. .................. | 435/135 |
| 2008/0200584 | A1 | 8/2008 | Bottcher et al. | |
| 2008/0293878 | A1 * | 11/2008 | Funk et al. ..................... | 524/588 |

FOREIGN PATENT DOCUMENTS

| | | |
|---|---|---|
| EP | 1502572 | 2/2005 |
| EP | 1502572 A1 * | 2/2005 |
| JP | 2000-73041 * | 3/2000 |
| WO | WO 9210544 A1 * | 6/1992 |
| WO | WO02/058641 | 8/2002 |

OTHER PUBLICATIONS

Abstract for JP 2000-73041 (Mar. 2000).*
Machine-generated translation for JP 2000-73041 (Mar. 2000).*
"In Situ Determination of the Active Catalyst in Hydrosilation Reactions Using Highly Reactive Pt(0) Catalyst Precursors" authored by Stein et al. and published in JACS (1999) 121, 3693-3703.*

* cited by examiner

*Primary Examiner* — Marc Zimmer
(74) *Attorney, Agent, or Firm* — Casimir Jones, S.C.

(57) ABSTRACT

A subject-matter of the invention is an impression material with at least one compound with at least two alkenyl groups as component (a), at least one compound with at least one chelating group as component (b), at least one organohydropolysiloxane as component (c), at least one hydrosilylation catalyst as component (d) and at least one compound with a chelatable metal atom as component (e), the chelating group of the component (b) exhibiting no reactive groups which can react with the component (c) and/or the component (d).
The invention achieves a long storage stability.

19 Claims, No Drawings

SILICON MOULDING MATERIAL COMPRISING A TWO-STAGE HARDENING MECHANISM

The present application is a 371 National Phase application of International Application No. PCT/IB2008/000092, filed Jan. 16, 2008, which claims priority to European Patent Application Ser. No. 06 023 846.6, filed Nov. 16, 2006, each of which is incorporated herein by reference in its entirety.

The invention relates to a multicomponent impression material which can pass through a mixer with a two-stage curing mechanism and also to the preparation thereof.

Multicomponent impression materials which can pass through a mixer with a two-stage curing mechanism, such as are used, inter alia, in dentistry, are known to a person skilled in the art, for example from WO 02/058641 and EP-A-1 502 572.

The materials which can pass through a mixer and which cure in two stages make it possible to discharge kneadable materials from automatic mixing and metering systems.

WO 02/058641 discloses a multicomponent system for the taking of impressions which comprises (a) at least one compound with at least two alkenyl groups, (b) at least one organohydropolysiloxane, (c) at least one hydrosilylation catalyst, ($d_1$) at least one polymeric compound with at least one alkynyl group and/or ($d_2$) at least one compound with at least one Si—OR structural unit, R being H, alkyl, alkoxyalkyl or acyl, and, in the presence of ($d_2$), (e) at least one condensation catalyst and/or condensation crosslinking agent. The compounds (a), (b), ($d_1$) and ($d_2$) are supplied in a component A and the compounds (c) and (e) are supplied in a component B, which are mixed with one another, for example by means of a dispenser (e.g., MixStar® or Pentamix®). In this connection, the mixture changes from a relatively thin starting consistency which can pass through a mixer to a more viscous plastic phase, in which the material is processed, e.g., to give the dental impression, before it, in a second stage, cures to give its final elastic form. At the beginning of the mixing, the mixture exhibits a consistency which can pass through a mixer of >30 mm according to ISO 4823, after which the mixture changes, by condensation reactions of Si—OR groups and/or by hydrosilylation reactions of alkynyl groups with SiH groups, to a second state with a consistency of <30 mm according to ISO 4823. In this state, which is usually described as heavy-bodied or putty consistency, the consistency remains virtually unchanged for a certain period of time. During this time, the mixture is processed, i.e. the impression is moulded. After that, the mixture changes, by a hydrosilylation reaction between alkenyl groups and SiH groups, to a third solid elastic state, in which the impression result is retained.

EP-A-1 502 572 discloses a similar multicomponent system which cures in two stages, in which, in a first step, a condensation reaction takes place and is followed, in a second step, by the addition reaction. Siloxanes are used with carbinol, carboxyl and amine groups in the condensation step.

It is an object of the invention to produce an impression material of the type mentioned at the start which is stable, in particular stable in the long term.

The invention achieves this object by an impression material with the characteristics of Claim 1. Advantageous embodiments of the invention are disclosed in the subclaims.

The invention has recognized that the combinations used for producing two-stage curing mechanisms described in WO 02/058641 and EP-A-1 502 572 comprise components carrying reactive groups which conceal a major disadvantage for the stability of the impression materials. These are silanol groups in the impression material of WO 02/058641 and hydroxyalkyl groups, amino groups or carboxyl groups in the impression material of EP-A-1 502 572. The components mentioned can react with the hydrosiloxanes which are always present in the impression materials as crosslinking agent components, with the splitting off of hydrogen. Thus, for example, the amino groups and carboxyl groups react in the abovementioned way in the presence of water, such as is incorporated, for example, via the filler component as traces of moisture. An additional disadvantage, recognized by the present invention, of amino groups and carboxyl groups is that they can interact with the platinum catalyst preferably used for addition reactions and can cause the addition crosslinking to be retarded, i.e. to have a delayed action, or to be completely inhibited. The stability, in particular the long-term stability, of the impression materials is impaired by this.

The invention has recognized that with a compound according to characteristic (b) of Claim 1, which exhibits no reactive groups, such as hydroxyalkyl groups, secondary amino groups or carboxyl groups, which can react with an organohydropolysiloxane or hydrosilylation catalyst, such as platinum, abovementioned undesirable reactions can be avoided and the stability of the impression materials can be guaranteed over a long period of time.

According to a preferred embodiment of the invention, the chelating group of the compound of the component (b) is a dicarbonyl group, in particular a 1,3-dicarbonyl group, such as a β-dicarboxylate or β-ketoester. Use is preferably made of compounds of the formulae

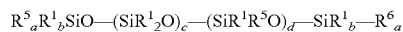

and

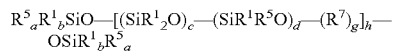

with
$R^1$=linear or branched alkyl, fluoroalkyl, cycloalkyl or aryl;
$R^2$=linear or branched alkylene, fluoroalkylene, cycloalkylene or arylene;
$R^3$=linear or branched alkylene with 1 to 10 carbon atoms, cycloalkylene or arylene;
$R^4$=linear or branched alkyl, cycloalkyl, aryl, $NR^1_2$, $NHR^1$ or alkoxy;
$R^5=R^4$—CO—$R^3_f$—CO—$X_e$—$R^2$—;
$R^6=R^4$—CO—$R^3_f$—CO—$X_e$—$R^2$;
$R^7=SiR^1_2$—$R^2$—$X_e$—CO—$R^3_f$—CO—$X_e$—$R^2$—$SiR^1_2$;
X=O or $NR^1$;
a=0 to 3; b=3−a; c=0 to 10 000; d=0 to 500; e=0 or 1; f=0 or 1; g=1 to 100 and h=1 to 1000.

Preferably, the impression material consists of at least one component B (base component) and one component C (catalyst component), the component B comprising the components (a), (b) and (c) and the component C comprising the components (d) and (e). The components B and C are, for example, pastes which are mixed in a mixing ratio of 10:1 to 1:1, particularly preferably 5:1.

Preferred alkenyl compounds (a) of the component B are those with the structure

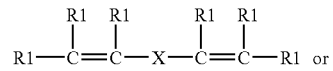 or

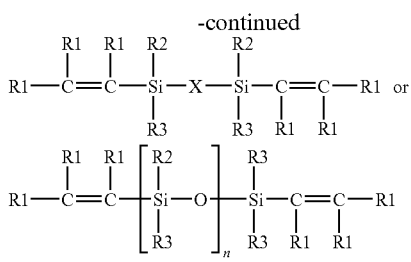

with n=0–20 000,

R1=H—, alkyl-, aryl-, arylalkyl-, halogen-substituted alkyl and aryl groups, cyanoalkyl-, cycloalkyl-, cycloalkenyl-, and combinations thereof;

R2=alkenyl-, alkynyl-, halo-, aryl-, alkylaryl-, H—, halogen-substituted alkyl and aryl groups, in particular alkyl-, and combinations thereof, R3=R2 or R3 is different from R2, R3 being in particular alkyl-, methyl-, alkynyl-, ethynyl- or combinations thereof, and X=polysiloxane, oligosilicic acid esters, polysilicic acid esters, polyethers, polymeric hydrocarbons, polyesters and copolymers of the abovementioned compounds.

The preferred alkenyl compound (a) can also be a silane dendrimer with end alkenyl groups or be present as a QM resin with at least one Si-alkenyl group.

Preferred organohydropolysiloxanes (c) which are present in the component B are polyalkyl-, polyaryl- and polyalkylaryl-, polyhaloalkyl-, polyhaloaryl- or polyhaloalkylarylsiloxanes. They can be present as oligomers or polymers in linear, branched or cyclic form or as QM resins and exhibit at least one Si—H bond. QM resins consist of Q units ($SiO_{4/2}$) and M units ($Me_3SiO_{1/2}$).

Preferred hydrosilylation catalysts (d) which are present in the component C are the transition metals of subgroup VIII, in particular platinum, palladium and rhodium or the salts, complexes and colloids thereof, preferably platinum complexes and salts of hexachloroplatinic acid, in particular the platinum (0) 1,3-divinyl-1,1,3,3-tetramethyldisiloxane complex.

Preferred compounds with a chelatable metal atom (e) which function as condensation catalysts or ligand exchange catalysts and are present in component C are alkoxymetal complexes $R_4Me$, preferably $R_4Ti$ or $R_4Zr$, and also the oligo- or polycondensates thereof.

Preferably, the components (a)-(e) are present in the impression material in the following constituent amounts:

10-60% by weight of component (a),
1-25% by weight of component (b),
0.2-10% by weight of component (c),
0.005-5% by weight of component (d) and
0.1-7% by weight of component (e).

In addition, the components B and C can comprise additional constituents, for example inhibitors of the addition reaction, which slow down the addition reaction or suppress it for a certain time, water-releasing agents, desiccants, inert carriers, reinforcing and nonreinforcing fillers, and additional auxiliaries.

Inhibitors of the addition reaction are, for example, disclosed in EP-A-1502572.

Use is preferably made, as water-releasing agents, of inorganic fillers, which comprise residual humidity bound at the surface or water bound in the crystal lattice, zeolites or specifically humidified fillers or organic materials with a defined water content.

Use is preferably made, as desiccants, of dried calcium sulphate, zeolites, dried fillers or water-absorbing organic compounds, such as oxazolidines and alkali metal salts of poly(meth)acrylic acid.

Use is preferably made, as inert carriers, of mineral oils, branched hydrocarbons, petrolatum, esters, phthalates, tributyl acetylcitrate, polyalkylene oxides and polyesters and the copolymers thereof.

Use is preferably made, as reinforcing fillers, of highly dispersed active fillers, such as titanium oxide, aluminium oxide, zinc oxide, pyrogenic or precipitated silica, fibrous mineral fillers, such as wollastonite, or fibrous synthetic fillers, such as glass fibres, ceramic fibres or plastic fibres.

The nonreinforcing fillers are preferably cristobalite, quartz, diatomaceous earth, zirconium silicate, calcium silicate, clay minerals, such as smectites, zeolites, sodium aluminium silicates, metal oxides, such as aluminium or zinc oxides, and the mixed oxides thereof, barium sulphate, calcium carbonate, glass powders, hollow glass spheres and plastic powders.

The filler can be, according to a preferred embodiment of the invention, a surface-modified filler, preferably a filler modified at the surface in organic fashion. The filler may, after its surface modification, for example a silanization, have functional groups on its surface.

In addition, the dental material according to the invention may, in order to adjust certain properties, comprise "additives" or "modifiers" as auxiliaries. Some examples are mentioned below, without being generally limiting: inorganic and/or organic colour pigments or dyes, stabilizers (such as, e.g., substituted and unsubstituted hydroxyaromatic compounds, Tinuvins, terpinenes, phenothiazine, "HALS" (Hindered Amine Light Stabilizers) and/or heavy metal scavengers, such as EDTA), plasticizers (such as, e.g., polyethylene glycols, polypropylene glycols, unsaturated polyesters, phthalates, adipates, sebacates, phosphoric acid esters, phosphoric acid esters and/or citric acid esters), ion-releasing substances, in particular those which release fluoride ions (such as, e.g., sodium fluoride, potassium fluoride, yttrium fluoride, ytterbium fluoride and/or quaternary ammonium fluorides), bactericides or antibiotically effective substances (such as, e.g., chlorhexidine, pyridinium salts, penicillins, tetracyclines, chloramphenicol, antibacterial macrolides and/or polypeptide antibiotics) and/or solvents (such as, e.g., water, acetone, ethanol, isopropanol, butanone and/or ethyl acetate).

The impression material can exhibit hydrophilic properties, e.g. if surfactants are added as auxiliary or if polyether groups are present.

The impression material can also comprise materials for adjusting the pH. These preferably include acetic acid, citric acid, tributyl acetylcitrate, ascorbic acid, acidic fillers, acidic buffer systems, such as acetic acid/sodium acetate buffer or citric acid/citrate buffer, and also basic fillers, such as, e.g., aluminium hydroxide, basic buffer systems, such as, e.g., carbonate/hydrogencarbonate buffer, or basic or acidic ion-exchange resins.

According to the invention, the impression material can pass through a mixer, i.e. the components B and C can, e.g. from a 2-component single-use cartridge, be mixed on a static mixer or a dispenser (e.g., MixStar® or Pentamix®) with a dynamic mixer and be discharged. Impression materials which can pass through a mixer in the abovementioned sense generally lie, at the beginning of the mixing time, according to ISO 4823, in the consistency range of greater than 26 mm, preferably greater than 30 mm. During and after the mixing of components B and C, the mixture changes in a first stage, which preferably takes place over a period of time of at least 15 seconds, particularly preferably 2 minutes, from its relatively thin starting consistency which can pass through a mixer to a more viscous plastic phase, before it cures, in a second stage, to give its final elastic form. In the first stage, the catalyst (e) acts on the chelating groups of the compound (b) and a ligand exchange reaction takes place which results in a degree of crosslinking (viscosity). The catalyst is, for example, an alkoxymetal complex $R_4Me$, preferably $R_4Ti$ or $R_4Zr$, which acts on the β-dicarboxylates or β-ketoesters.

In the second step, complete crosslinking then takes place by an addition reaction of the organohydropolysiloxanes (c) with the compound with at least two alkenyl groups (a), preferably using a platinum catalyst (d). The components are preferably chosen in such a way that the ligand exchange reaction and the addition reaction take place at 10 to 40° C., so that the reactions can be carried out in particular at mouth and ambient temperature.

The invention comprises the impression material according to the invention in all states described, including after the mixing, in particular after the mixing of components B and C, and the curing. The mixture in the cured state preferably fulfils the requirements placed according to ISO 4823 on an elastomeric impression material in the cured state, such as, for example, the recovery after deformation.

According to the invention, the components B and C are stable on storage for more than 3 months, preferably more than 6 months, more preferably more than 12 months, particularly preferably more than 24 months. Stable on storage within the meaning of the present invention means that, under normal storage conditions (ambient temperature, dry storage), no decline in the reaction capabilities occurs, in particular no decline in the reaction capabilities occurs which is accompanied by a deterioration in the mechanical properties of the impression material.

The invention also relates to a process for the preparation of impressions of objects, an impression of which is to be taken.

According to the invention, in the process, in a first step, the components (a)-(e) of the impression material according to the invention are mixed, in a second step, the mixture is brought into contact with a surface of an object, an impression of which is to be taken, and, subsequently, the impression is removed.

Preferably, in the first step, the components B and C are discharged from a container, for example a cartridge, over a mixer and mixed. During the mixing operation and afterwards, the mixture changes to a first state, which continues over the processing time (preferably at least 15 seconds), in which the viscosity of the impression material is increased (heavy-bodied to putty consistency), after which an impression is taken of the object, an impression of which is to be taken. Subsequently, the impression material changes to a next, solid and elastic state, in which the impression result is maintained, so that the impression can be removed from the object.

The invention is illustrated below with exemplary embodiments, without limitation on the general nature. The values, if not further specified, were determined according to ISO 4823.

I. EXAMPLES ACCORDING TO THE INVENTION

Example 1

Preparation of Polydimethylsiloxanes Comprising Chelate Groups 500 g of Tegomer HSi 2311 (α,ω-hydroxyalkylpolydimethyl-siloxane, 200 mmol, Goldschmidt) and 66.3 g of tert-butyl acetoacetate (419 mmol, Fluka) are heated with stirring in a two-necked flask at 140° C. for 3 h. During this time, tert-butanol produced is distilled off. The reaction mixture is cooled down and volatile constituents are removed under vacuum at 0.1 mbar and 55° C. Yield: 527.54 g. Polydimethylsiloxane modified with acetoacetic ester (FT-IR, proton NMR).

Example 2

Preparation of Polydimethylsiloxanes Comprising Chelate Groups 23.31 g of Tegomer HSi 2311 (9 mmol, Goldschmidt) are diluted with 20 ml of distilled toluene in a two-necked flask with a dropping funnel and a $CaCl_2$ drying tube.

1.52 ml of distilled pyridine (18 mmol) are added with stirring. 2 ml of ethyl malonyl chloride (18 mmol, Fluka) are diluted with 5 ml of distilled toluene in the dropping funnel. This solution is slowly added dropwise, via the dropping funnel, to the mixture of Tegomer HSi 2311, pyridine and toluene. After the end of the addition, the mixture is stirred overnight at AT. The precipitate produced is filtered off. The organic phase is extracted twice with 10 ml of saturated $NaHCO_3$. Subsequently, the organic phase is dried over $Na_2SO_4$. Toluene is removed on a rotary evaporator and the residue is freed from volatile constituents under vacuum at 0.08 mbar and 50° C. Yield: 17.2 g of polydimethylsiloxane modified with monomethyl malonate (FT-IR, proton NMR).

Example 3

Each 1 g of polydimethylsiloxane modified with acetoacetic ester from Example 1 is treated with different amounts of tetra(n-propyl) zirconate (Tyzor NPZ, Du Pont) according to the following Examples 3.1, 3.2, 3.3 and 3.4. The viscosity of the mixture is measured on a rheometer at a shear stress of 500 Pa (DSR from Rheometrics, geometry: parallel plate, diameter: 25 mm, gap width: 0.1 mm, temperature: 23° C.)

|  | Example 3.1 | Example 3.2 | Example 3.3 | Example 3.4 |
| --- | --- | --- | --- | --- |
| PDMS modified with acetoacetic ester | 1 g | 1 g | 1 g | 1 g |
| Tyzor NPZ | — | 0.05 g | 0.1 g | 0.2 g |
| Viscosity [Pa · s] | 0.06 | 0.18 | 0.63 | 15 693 |

With an increasing proportion of tetra(n-propyl)zirconate, more metal atoms are also available which can be complexed by the chelate groups. Because of this, the molecular weight or the chain length of the polymers is increased, which is reflected in the increase in viscosity.

Example 4

Preparation of a Base Paste 1 (B1)

17.5% by weight of a vinyl-stopped polydimethylsiloxane (65 000 mPa·s, vinyl content 0.03 mmol/g), 4.3% by weight of a vinyl-stopped polydimethylsiloxane (1 650 000 mPa·s, vinyl content 0.02 mmol/g), 2.2% by weight of a methyl-stopped polydimethylsiloxane (1000 mPa·s), 0.2% by weight of a polyhydromethylsiloxane (230 mPa·s, SiH content 2.3 mmol/g), 0.6% by weight of a polyhydromethylsiloxane (40 mPa·s, SiH content 4.3 mmol/g), 3.9% by weight of petrolatum, 6.0% by weight of paraffin and 10% by weight of polydimethylsiloxane modified with acetoacetic ester from Example 1 according to the invention are introduced into a laboratory mixer. 16.5% by weight of diatomaceous earth, 37.2% by weight of powdered hydrophobized cristobalite, 1% by weight of hydrophobized pyrogenic silica (BET specific surface 140 m$^2$/g) and 0.6% by weight of an ultramarine pigment are incorporated in this mixture and the mixture is stirred until homogeneous.

Example 5

Preparation of a Catalyst Paste 1 (C1)

5.7% by weight of a vinyl-stopped polydimethylsiloxane (1000 mPa·s, vinyl content 0.13 mmol/g), 12.7% by weight of a vinyl-stopped polydimethylsiloxane (65 000 mPa·s, vinyl content 0.03 mmol/g), 5.7% by weight of a vinyl-stopped polydimethylsiloxane (1 650 000 mPa·s, vinyl content 0.02 mmol/g), 2.4% by weight of a methyl-stopped polydimethylsiloxane (1000 mPa·s), 3.8% by weight of petrolatum, 5.7% by weight of paraffin, 15.1% by weight of diatomaceous earth, 41.9% by weight of powdered hydrophobized cristobalite, 0.18% by weight of titanium dioxide, 0.02% by weight of 1,3-divinyl-1,1,3,3-tetramethyldisiloxane, 0.8% by weight of a platinum catalyst, dissolved in a vinyl-stopped polydimethylsiloxane (1000 mPa·s, vinyl content 0.13 mmol/g, platinum content of the solution=2% by weight), and 6.0% by weight of tetra(n-propyl) zirconate (Tyzor NPZ, Du Pont) are mixed in a laboratory mixer until homogeneous.

Example 6

Preparation of a Catalyst Paste 2 (C2)

5.7% by weight of a vinyl-stopped polydimethylsiloxane (1000 mPa·s, vinyl content 0.13 mmol/g), 12.7% by weight of a vinyl-stopped polydimethylsiloxane (65 000 mPa·s, vinyl content 0.03 mmol/g), 5.6% by weight of a vinyl-stopped polydimethylsiloxane (1 650 000 mPa·s, vinyl content 0.02 mmol/g), 2.4% by weight of a methyl-stopped polydimethylsiloxane (1000 mPa·s), 3.8% by weight of petrolatum, 5.7% by weight of paraffin, 15.1% by weight of diatomaceous earth, 41.8% by weight of powdered hydrophobized cristobalite, 0.18% by weight of titanium dioxide, 0.02% by weight of 1,3-divinyl-1,1,3,3-tetramethyldisiloxane, 0.8% by weight of a platinum catalyst, dissolved in a vinyl-stopped polydimethylsiloxane (1000 mPa·s, vinyl content 0.13 mmol/g, platinum content of the solution=2% by weight), and 6.2% by weight of tetra(n-butyl) titanate (Tyzor TnBT, Du Pont) are mixed in a laboratory mixer until homogeneous.

Example 7

When mixed by hand (mixing on a smooth support using a standard dental spatula), the following values were determined for the pastes B1, C1 and C2 of Examples 4-6 according to the invention and the mixtures thereof:
Consistency B1: 31 mm
Consistency C1: 32 mm
Consistency C2: 33 mm
Mixed consistency 5 parts B1+1 part C1: 21 mm
Mixed consistency 5 parts B1+1 part C2: 22.5 mm
Processing latitude 5 parts B1+1 part C1: 3:15-3:30 min:sec (incl. 1 min mixing time)

Processing latitude 5 parts B1+1 part C2: 3:00 min:sec (incl. 1 min mixing time)
Setting time 5 parts B1+1 part C1: 4:30 min:sec (incl. 1 min mixing time)
Setting time 5 parts B1+1 part C2: 4:00-4:15 min:sec (incl. 1 min mixing time)
The following values were determined from the cartridge:
from cartridge (5 parts B1+1 part C2) with 15 mm/min (MixStar® mixing system, DMG) feeding: maximum temperature on mixing: 31.5° C.
from cartridge (5 parts B1+1 part C2) with 24 mm/min feeding (Pentamix®, 3M ESPE): maximum temperature on mixing: 31.5° C.

Example 8

Preparation of a Base Paste 2 (B2)

24.1% by weight of a vinyl-stopped polydimethylsiloxane (65 000 mPa·s, vinyl content 0.03 mmol/g), 0.7% by weight of a polyhydromethylsiloxane (40 mPa·s, SiH content 4.3 mmol/g), 3.9% by weight of petrolatum, 6.1% by weight of paraffin and 10% by weight of polydimethylsiloxane modified with acetoacetic ester from Example 1 are introduced into a laboratory mixer. 16.5% by weight of diatomaceous earth, 38.1% by weight of powdered hydrophobized cristobalite and 0.6% by weight of an ultramarine pigment are incorporated in this mixture and the mixture is stirred until homogeneous.

Example 9

Preparation of a Catalyst Paste 3 (C3)

8.0% by weight of a vinyl-stopped polydimethylsiloxane (1000 mPa·s, vinyl content 0.13 mmol/g), 12.7% by weight of a vinyl-stopped polydimethylsiloxane (65 000 mPa·s, vinyl content 0.03 mmol/g), 5.6% by weight of a vinyl-stopped polydimethylsiloxane (1 650 000 mPa·s, vinyl content 0.02 mmol/g), 3.8% by weight of petrolatum, 5.6% by weight of paraffin, 15.1% by weight of diatomaceous earth, 42.2% by weight of powdered hydrophobized cristobalite, 0.02% by weight of 1,3-divinyl-1,1,3,3-tetramethyldisiloxane, 0.78% by weight of a platinum catalyst, dissolved in a vinyl-stopped polydimethylsiloxane (1000 mPa·s, vinyl content 0.13 mmol/g, Pt content of the solution=2% by weight), and 6.2% by weight of tetra(n-butyl) titanate (Tyzor TnBT, Du Pont) are mixed in a laboratory mixer until homogeneous.

Example 10

When mixed by hand, the following values were determined for the pastes B2 and C3 of Examples 8 and 9 according to the invention and the mixture thereof:
Consistency B2: 29.5 mm
Consistency C3: 34 mm
Processing latitude 5 parts B2+1 part C3: 4:45 min:sec (incl. 1 min mixing time)
Setting time 5 parts B2+1 part C3: 4:45-5:00 min:sec (incl. 1 mixing time)
Shore A after 24 h 5 parts B2+1 part C3: 36
The following values were determined from the cartridge:
From cartridge (5 parts B2+1 part C3) with 15 mm/min feeding:
Processing latitude: 3:30 min:sec (incl. 1 min mixing time)
Setting time: 5:00 min:sec (incl. 1 min mixing time)
Lasting deformation: 1.3%

Deformation under pressure: 6.3%
Mixed consistency: 24 mm
Maximum temperature on mixing: 31.0° C.

As clear from the values determined for Examples 7 and 10, the base and catalyst pastes according to the invention are suitable for manual mixing and for use in conventional cartridges and exhibit processing parameters such as are desired in particular in dental applications.

II. COMPARATIVE EXAMPLES

Not According to the Invention

Base and catalyst pastes for an impression material which crosslinks by addition not according to the invention are prepared as follows:

Example 11

Preparation of a Base Paste 1 (B1)

19.0% by weight of a vinyl-stopped polydimethylsiloxane (1000 mPa·s, vinyl content 0.13 mmol/g), 21.7% by weight of a vinyl-stopped polydimethylsiloxane (10 000 mPa·s, vinyl content 0.05 mmol/g), 10.9% by weight of a methyl-stopped polydimethylsiloxane (10 mPa·s), 6.0% by weight of a polyhydromethylsiloxane (230 mPa·s, SiH content 2.3 mmol/g), 0.2% by weight of an ultramarine pigment, 4.3% by weight of a hydrophobized pyrogenic silica (BET specific surface 140 m²/g) and 37.9% by weight of a powdered hydrophobized cristobalite are mixed in a laboratory mixer until homogeneous.

Example 12

Preparation of a Catalyst Paste 1 (C1)

22.4% by weight of a vinyl-stopped polydimethylsiloxane (1000 mPa·s, vinyl content 0.13 mmol/g), 22.4% by weight of a vinyl-stopped polydimethylsiloxane (10 000 mPa·s, vinyl content 0.05 mmol/g), 11.2% by weight of a methyl-stopped polydimethylsiloxane (10 mPa·s), 0.3% by weight of a platinum catalyst, dissolved in a vinyl-stopped polydimethylsiloxane (1000 mPa·s, vinyl content 0.13 mmol/g, Pt content of the solution=2% by weight), 4.5% by weight of a hydrophobic pyrogenic silica (BET specific surface 140 m²/g) and 39.2% by weight of a powdered hydrophobic cristobalite are mixed in a laboratory mixer until homogeneous.

Example 13

Preparation of a Base Paste 2 (B2)

92.5% by weight of the base paste 1 from Example 11 was mixed in a laboratory mixer with 7.5% by weight of the polydimethylsiloxane comprising amino groups Tego IS 4111 (Goldschmidt) until homogeneous.

Example 14

Preparation of a Catalyst Paste 2 (C2)

92.5% by weight of the catalyst paste 1 from Example 12 was mixed in a laboratory mixer with 7.5% by weight of the polydimethylsiloxane comprising amino groups Tego IS 4111 until homogeneous.

Example 15

Cross Experiments with the Pastes B1, C1, B2 and C2 of Examples 11-14

In a cross experiment, the base and catalyst pastes B1, C1, B2 and C2 of the abovementioned Comparative Examples 11-14 were mixed in the ratio by weight 1:1 and the processing latitude and the setting time after preparation and also after storage at 23° C. were determined (see following table). In these tests, the influence of the amino functional group on silicones which crosslink by addition is to be investigated.

| Combination | after preparation | | after storage[a)] | |
|---|---|---|---|---|
| | Processing latitude[b)] | Setting time[c)] | Processing latitude[b)] | Setting time[c)] |
| B1 + C1 (control) | 3:15 min:sec | 4:30 min:sec | 2:45-3:00 min:sec | 4:00 min:sec |
| B1 + C2 | not determined | ca. 180 min | ca. 120 min | <16 h |
| B2 + C1 | not determinable | no curing | not determinable | no curing |
| B2 + C2 | not determinable | no curing | not determinable | no curing |

[a)]Duration of storage 83 days
[b)]incl. 1:00 min:sec mixing time, measured at 23° C.
[c)]incl. 1:00 min:sec mixing time, measured at 32° C.

The following conclusions can be drawn from the tests of the cross experiment:

If the catalyst paste comprises a compound with amino groups (C2), a hardening takes place which is clearly slowed down (B1+C2) or hardening does not take place at all (B2+C2), with reference to the control not comprising amino groups (B1+C1). The cause is assumed to be an interaction, mentioned at the start, of the amino groups with the Pt atom of the platinum catalyst, so that the hydrosilylation of the vinyl groups proceeds only very slowly. If the base paste comprises a compound with amino groups (B2), the mixed pastes no longer cure (B2+C1 and B2+C2).

Example 16

Preparation of a Base Paste 3 (B3)

The base paste 3 of the present Comparative Example 16 corresponds, in the preparation and composition, to the base paste 1 of Example 4 according to the invention, with the difference that the 10% by weight of the polydimethylsiloxane modified with acetoacetic ester has been replaced by the polydimethylsiloxane modified with amino groups Tego IS 4111.

Example 17

Preparation of a Catalyst Paste 3 (C3)

The catalyst paste 3 of the present Comparative Example 17 corresponds, in the preparation and composition, to the catalyst paste 1 of Example 5 according to the invention.

Example 18

When mixed by hand, the following values were determined for the pastes B3 and C3 of Comparative Examples 16 and 17 and the mixture thereof:
Consistency B3: 29 mm
Consistency C3: 36 mm
Mixed consistency 5 parts B3+1 part C3: 20 mm Processing latitude 5 parts B3+1 part C3: 3: not ascertainable (incl. 1 min mixing time)

Setting time 5 parts B3+1 part C3: >40 min (incl. 1 min mixing time)

In contrast to the mixtures of Examples 7 and 10 according to the invention, no useable two-stage curing mechanism could be detected in the present comparative example after the mixing of the two pastes B3 and C3. The processing latitude is undetectable and the setting time is too slow.

The invention claimed is:

1. Impression material with
   a) at least one compound with at least two alkenyl groups as component (a),
   b) at least one compound with at least one chelating group as component (b),
   c) at least one organohydropolysiloxane as component (c),
   d) at least one hydrosilylation catalyst as component (d) and
   e) at least one compound with a chelatable metal atom as component (e),
   wherein the chelating group of the component (b) exhibits no reactive groups which can react with the component (c) and/or the component (d).

2. Impression material according to claim 1, wherein the chelating group of the compound of the component (b) is a dicarbonyl group.

3. Impression material according to claim 1, wherein the chelating group of the component (b) exhibits no reactive groups chosen from the group consisting of hydroxylalkyl group, amino group and carboxyl group.

4. Impression material according to claim 1 or claim 2, wherein the impression material consists of at least two components B and C, the component B comprising the components (a), (b) and (c) and the component C comprising the components (d) and (e).

5. Impression material according to claim 4, wherein the components B and C are stable on storage for more than 3 months.

6. Impression material which can be obtained by mixing the components B and C according to claim 4.

7. Impression material according to claim 5, wherein, during the mixing and/or after the mixing of the components B and C, the mixture changes, in a first stage, from a relatively thin starting consistency which can pass through a mixer to a more viscous plastic phase, before it cures, in a second stage, to give its final elastic form.

8. Cured impression material, which can be obtained from an impression material according to claim 1 or claim 2.

9. Process for the preparation of an impression of an object, an impression of which is to be taken, wherein an impression material according to claim 1 or claim 2 is used, in which, in a first step, the components (a)-(e) are mixed, in a second step, the mixture is brought into contact with a surface of an object, an impression of which is to be taken, and, subsequently, the impression is removed.

10. The process of claim 9, characterized in that $R^1$ is a methyl group.

11. The process of claim 9 or 10, characterized in that $R^3$ is a methylene group.

12. Impression material according to claim 1 or claim 2, wherein the chelating group of the compound of the component (b) is a 1,3-dicarbonyl group.

13. Impression material according to claim 1 or claim 2, wherein the compound of component (b) is as a β-dicarboxylate or β-ketoester.

14. Impression material of claim 1 or claim 2, wherein the compounds of component (b) are compounds of the formulae

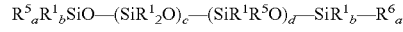

and

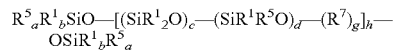

with
   $R^1$=linear or branched alkyl, fluoroalkyl, cycloalkyl or aryl;
   $R^2$=linear or branched alkylene, fluoroalkylene, cycloalkylene or arylene;
   $R^3$=linear or branched alkylene with 1 to 10 carbon atoms, cycloalkylene or arylene;
   $R^4$=linear or branched alkyl, cycloalkyl, aryl, $NR^1_2$, $NHR^1$ or alkoxy;
   $R^5=R^4-CO-R^3_f-CO-X_e-R^2-$;
   $R^6=R^4-COR^3_f-CO-X_e-R^2$;
   $R^7=SiR^1_2-R^2-X_e-CO-R^3_f-CO-X_e-R^2-SiR^1_2$;
   X=O or $NR^1$; and
   a=0 to 3; b=3-a; c=0 to 10 000; d=0 to 500; e=0 or 1; f=0 or 1; g=1 to 100 and h=1 to 1000.

15. Impression material according to claim 14, wherein $R^1$ is a methyl group.

16. Impression material according to claim 14, wherein $R^3$ is a methylene group.

17. Impression material according to claim 5, wherein the components B and C are stable on storage for more than 6 months.

18. Impression material according to claim 17, wherein the components B and C are stable on storage for more than 12 months.

19. Impression material according to claim 18, wherein the components B and C are stable on storage for more than 24 months.

* * * * *